(12) United States Patent
Utter et al.

(10) Patent No.: US 10,159,486 B2
(45) Date of Patent: Dec. 25, 2018

(54) FENESTRATED DECOUPLING SYSTEM FOR INTERNAL SELECTIVE ATTACHMENT TO SOFT TISSUE ORGANS

(71) Applicant: THE REGENTS OF THE UNIVERSITY OF MICHIGAN, Ann Arbor, MI (US)

(72) Inventors: Brent Utter, Easton, PA (US); Jennifer Freeman, Cambridge, MA (US); Daniel H. Teitelbaum, Ann Arbor, MI (US); Diann Erbschloe Brei, Milford, MI (US); Jonathan E. Luntz, Ann Arbor, MI (US); Yumi Fukatsu, Tokyo (JP); Farokh R. Demehri, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 216 days.

(21) Appl. No.: 14/718,175

(22) Filed: May 21, 2015

(65) Prior Publication Data

US 2015/0335331 A1    Nov. 26, 2015

Related U.S. Application Data

(60) Provisional application No. 62/001,380, filed on May 21, 2014.

(51) Int. Cl.
*A61B 17/11* (2006.01)
*A61B 17/12* (2006.01)
(Continued)

(52) U.S. Cl.
CPC .......... *A61B 17/1114* (2013.01); *A61B 17/02* (2013.01); *A61B 17/12136* (2013.01);
(Continued)

(58) Field of Classification Search
CPC ................ A61B 17/1114; A61B 17/02; A61B 17/12136; A61B 17/12131;
(Continued)

(56) References Cited

U.S. PATENT DOCUMENTS

| 4,840,690 A | 6/1989 | Melinyshyn et al. |
| 4,950,226 A | 8/1990 | Barron |

(Continued)

FOREIGN PATENT DOCUMENTS

| EP | 1796553 A2 | 6/2007 |
| SU | 1650147 A1 | 5/1991 |

(Continued)

OTHER PUBLICATIONS

International Search Report and Written Opinion regarding PCT/US2016/014688 dated Jun. 10, 2016.

(Continued)

*Primary Examiner* — Jocelin Tanner
(74) *Attorney, Agent, or Firm* — Harness, Dickey & Pierce, P.L.C.

(57) ABSTRACT

An attachment system for selectively attaching to an interior surface of a hollow member, which includes an expanding device selectively enlargeable from a first size position to an enlarged second size position, a friction enhancement disposed about the expanding device that is engageable with the interior surface of the hollow member when the expanding device is in the enlarged position, and a fenestrated decoupling system extending between at least a portion of the friction enhancement of the expanding device and the interior surface of the hollow member. The fenestrated decoupling system generally prevents contact of the friction enhancement with the interior surface of the hollow member when the expanding device is in the first size position and permits contact of the friction enhancement with the interior (Continued)

surface of the hollow member when the expanding device is in the enlarged position.

17 Claims, 8 Drawing Sheets

(51) Int. Cl.
　　A61M 29/02　　(2006.01)
　　A61B 17/02　　(2006.01)
　　A61B 90/00　　(2016.01)
　　A61B 17/00　　(2006.01)
(52) U.S. Cl.
　　CPC ............ *A61B 90/02* (2016.02); *A61M 29/02* (2013.01); *A61B 17/12045* (2013.01); *A61B 2017/00367* (2013.01); *A61B 2017/00557* (2013.01); *A61B 2017/00818* (2013.01); *A61B 2017/1135* (2013.01); *A61B 2017/12054* (2013.01); *A61B 2017/12127* (2013.01)
(58) Field of Classification Search
　　CPC ........ A61B 17/12045; A61B 17/12022; A61B 17/12027; A61B 17/12031; A61B 17/12036; A61B 17/1204; A61B 2017/00557; A61B 2017/00818; A61B 2017/12127; A61B 2017/00367; A61B 2017/1135; A61B 2017/12054; A61B 2017/22051; A61B 2017/22054; A61B 2017/22061; A61B 2017/22067; A61B 2017/22069; A61B 2017/3486; A61B 2017/3488; A61B 1/00082; A61B 1/00085; A61B 2018/0025; A61B 2018/00273; A61B 2018/00285; A61B 2018/00291; A61M 29/02
　　See application file for complete search history.

(56) References Cited

U.S. PATENT DOCUMENTS

| | | |
|---|---|---|
| 5,161,547 A * | 11/1992 | Tower .................. A61F 2/88 128/898 |
| 5,205,830 A | 4/1993 | Dassa et al. |
| 5,211,654 A * | 5/1993 | Kaltenbach ......... A61M 25/104 604/913 |
| 5,364,396 A | 11/1994 | Robinson et al. |
| 5,415,660 A | 5/1995 | Campbell et al. |
| 5,634,901 A | 6/1997 | Alba et al. |
| 5,662,583 A | 9/1997 | Khouri |
| 5,681,309 A | 10/1997 | Ross, Jr. et al. |
| 5,693,014 A | 12/1997 | Abele et al. |
| 5,700,252 A | 12/1997 | Klingenstein |
| 5,769,870 A | 6/1998 | Salahieh et al. |
| 5,836,864 A | 11/1998 | Clark, Jr. |
| 5,902,304 A | 5/1999 | Walker et al. |
| 5,911,715 A | 6/1999 | Berg et al. |
| 5,916,193 A | 6/1999 | Stevens et al. |
| 5,947,104 A | 9/1999 | Li |
| 6,030,386 A | 2/2000 | Taylor et al. |
| 6,293,920 B1 | 9/2001 | Sweezer et al. |
| 6,319,233 B1 | 11/2001 | Jansen et al. |
| 6,336,929 B1 | 1/2002 | Justin |
| 6,355,031 B1 * | 3/2002 | Edwards ................ A61B 18/12 606/102 |
| 6,358,283 B1 | 3/2002 | Hogfors et al. |
| 6,368,315 B1 | 4/2002 | Gillis et al. |
| 6,375,638 B2 | 4/2002 | Nason et al. |
| 6,402,859 B1 | 6/2002 | Ishii et al. |
| 6,673,079 B1 | 1/2004 | Kane |
| 6,678,562 B1 | 1/2004 | Tepper et al. |
| 6,702,802 B1 | 3/2004 | Hancock et al. |
| 6,752,808 B2 | 6/2004 | Schumacher |
| 6,786,910 B2 | 9/2004 | Cohen et al. |
| 6,835,207 B2 | 12/2004 | Zacouto et al. |
| 7,018,402 B2 | 3/2006 | Vito et al. |
| 8,048,028 B2 | 11/2011 | Horn et al. |
| 8,177,743 B2 | 5/2012 | Lennox |
| 8,268,009 B2 | 9/2012 | Teitelbaum et al. |
| 8,388,674 B2 | 3/2013 | Sandhu et al. |
| 2002/0095120 A1 | 7/2002 | Larsen et al. |
| 2004/0087827 A1 * | 5/2004 | Lubock ................ A61N 5/1015 600/3 |
| 2005/0010191 A1 | 1/2005 | Skinner et al. |
| 2006/0052753 A1 | 3/2006 | Mansouri |
| 2006/0069403 A1 | 3/2006 | Shalon et al. |
| 2006/0079897 A1 | 4/2006 | Harrison et al. |
| 2006/0189899 A1 | 8/2006 | Flaherty et al. |
| 2007/0119165 A1 | 5/2007 | Yson et al. |
| 2007/0219466 A1 | 9/2007 | Tremulis et al. |
| 2008/0200839 A1 | 8/2008 | Bunch et al. |
| 2010/0114017 A1 | 5/2010 | Lenker et al. |
| 2011/0152683 A1 * | 6/2011 | Gerrans ............ A61B 17/22012 600/435 |
| 2011/0224625 A1 | 9/2011 | Flickinger et al. |
| 2011/0295234 A1 | 12/2011 | Eaton |
| 2012/0016342 A1 | 1/2012 | Brecker |
| 2012/0059401 A1 | 3/2012 | Konstantino et al. |
| 2012/0083820 A1 | 4/2012 | Carman et al. |
| 2012/0095385 A1 | 4/2012 | Dominguez et al. |
| 2012/0289982 A1 * | 11/2012 | Gunday ......... A61B 17/320725 606/159 |
| 2013/0030425 A1 | 1/2013 | Stewart et al. |
| 2013/0041244 A1 | 2/2013 | Woias et al. |
| 2013/0066155 A1 | 3/2013 | Keating et al. |
| 2013/0116655 A1 * | 5/2013 | Bacino ........... A61B 17/320725 604/509 |
| 2013/0253426 A1 | 9/2013 | Campbell et al. |
| 2013/0289498 A1 | 10/2013 | Bosma |
| 2014/0066898 A1 | 3/2014 | Cully et al. |
| 2014/0088362 A1 | 3/2014 | Terliuc et al. |
| 2015/0081006 A1 | 3/2015 | Chuter et al. |

FOREIGN PATENT DOCUMENTS

| | | |
|---|---|---|
| SU | 1814906 A1 | 5/1993 |
| WO | 9114395 A1 | 10/1991 |
| WO | 2010/124126 A2 | 10/2010 |
| WO | 2014028922 A2 | 2/2014 |

OTHER PUBLICATIONS

International Search Report and Written Opinion regarding PCT/US2015/031956 dated Aug. 28, 2015.
Early Commercial Assessment for Discussion, May 7, 2014, "Organ Repair, Hemostasis, and In Vivo Bonding of Medical Devices by Aqueous Solutions of Nanoparticles," Meddahi-Pellé, Ann et al.
Journal of Pediatric Surgery, vol. 38, No. 6 Jun. 2003, p. 881-885 "Serial Transverse Enteroplasty for Short Bowel Syndrome: A Case Report", Heung Bae Kim et al.
American Pediatric Surgical Association, May 2002, p. 1085-1090 "Longitudinal Mechanical Tension Induces Growth in the Small Bowel of Juvenile Rats", S. D. Safford et al.
Journal of the Royal Society of Medicine, vol. 90, Aug. 1997, pp. 429-432, "Longitudinal Intestinal Lengthening and Tailoring: Results in 20 Children", A. Bianchi M.D.
Journal of the Royal Society of Medicine, Supplement No. 3, vol. 77, 1984, pp. 35-41, "Intestinal Lengthening: An Experimental and Clinical Review", A. Bianchi M.D. et al.
Scandinavian Journal of Gastroenterology, pp. 48-54, "Effect of High-Dose Growth Hormone and Glutamine on Body Composition, Urine Creatinine Excretion, Fatty Acid Absorption, and Essential Fatty Acids Status in Short Bowel Patients", P. B. Jeppesen et al.
The Endocrine Society, vol. 138, No. 11, pp. 4837-4843, "Circulating and Tissue Forms of the Intestinal Growth Factor, Glucagon-Like Peptide-2", Patricia L. Brubaker et al.
Journal of Pediatric Surgery, vol. 36, No. 1 Jan. 2001, pp. 178-183, "Analysis of Patients With Longitudinal Intestinal Lengthening Procedure Referred for Intestinal Transplantation", Javier Bueno et al.

(56) References Cited

OTHER PUBLICATIONS

Journal of Surgical Research 77, Article No. JR985362, (1998) pp. 17-22, "The EGF/EGF-Receptor Axis Modulates Enterocyte Apoptosis During Intestinal Adaption", Michael A. Helmrath, M.D. et al.
The Journal of Immunology, vol. 172, pp. 4151-4158, 2004, "Intestinal Intraepithelial Lymphocyte T Cell-Derived Keratinocyte Growth Factor Modulates Epithelial Growth in the Mouse", Hua Yang et al.
The American Gastroenterological Association, vol. 130, pp. 117-121, 2006, "Novel Agents in the Treatment of Intestinal Failure: Humoral Factors", Hua Yang et al.
Journal of Pediatric Surgery, vol. 41, pp. 763-767, 2006, "Distension Enterogenesis: Increasing the Size and Function of Small Intestine," Devin P. Puapong et al.
Journal of Surgical Research, vol. 170, No. 1, Sep. 2011, Association for Academic Surgery, "Distraction Induced Enterogenesis: A Unique Mouse Model Using Polyethylene Glycol," Manabu Okawada, M.D. et al.
Annals of Surgery, vol. 255, No. 2, pp. 302-310, Feb. 2012, "Distraction-Induced Intestinal Enterogenesis—Preservation of Intestinal Function and Lenghthening after Reimplantation into Normal Jejunum," Hiroyuki Koga, M.D. et al.
Journal of Pediatric Surgery, vol. 39, No. 12, pp. 1823-1827, Dec. 2004, "Enterogenesis by Mechanical Lengthening: Morphology and Function of the Lenthened Small Intestine," Jinyoung Park et al.
Surgery Journal, vol. 140, No. 2, pp. 212-220, 2006, "Enterogenesis in a Clinically Feasible Model of Mechanical Small-Bowel Lengthening," Ariel U. Spencer, M.D. et al.
Journal of Surgical Research, pp. 1-6, Apr. 2011, "Flow Through a Mechanical Distraction Enterogenesis Device: A Pilot Test," Eiichi A. Miyasaka, M.D. et al.
International Conference on Adaptive Structures and Technologies, Oct. 2011, "Design and In Vivo Validation of an Implantable SMA Driven Bowel Extender for Correcting Short Bowel Syndrome," Brent Utter et al.
Proceedings of SPIE, vol. 6173, 617309, 2006, "Mechanical Extension Implants for Short-Bowel Syndrome," Jonathan Luntz et al.
Journal of Pediatric Surgery, vol. 46, pp. 2321-2326, 2011, "Restoration of Mechanically Lengthened Jejunum into Intestinal Continuity in Rats," Rebecca Stark et al.
Digestion, vol. 58, pp. 240-248, 1997, "Small Bowel Lengthening by Mechanical Distraction," Hartmut Printz, M.D. et al.
Proceedings of ASME 2010 Conference on SMASIS2010-3895, 2010, "Design of an SMA Actuated Mechanotransductive Implant for Correcting Short Bowel Syndrome," Brent Utter et al.
Journal of Pediatric Surgery, vol. 41, pp. 2019-2022, 2006, "Sustainability of Mechanically Lengthened Bowel in Rats," Paul C.Y. Chang et al.
Journal of Pediatric Surgery, vol. 45, pp. 1575-1580, 2010, "The Feasibility of Using an Endoluminal Device for Intestinal Lengthening," Shant Shekherdimian et al.
Journal of Surgical Research, vol. 163, No. 2, pp. 169-175, 2010, "Association for Academic Surgery, Application of Distractive Forces to the Small Intestine: Defining Safe Limits," Eiichi A. Miyasaka, M.D. et al.
ECCOMAS Conference on Smart Structures and Materials, SMART2013, Jun. 2013, "A Shape Memory Alloy Driven and Instrumented Bowel Extending Device for Investigating the Mechanotransduction Based Approach to Correcting Short Bowel Syndrome," Brent Utter et al.
Journal of Pediatric Surgery, vol. 47, pp. 136-141, 2012, "Development of an Endoluminal Intestinal Lengthening Capsule," Rebecca Stark et al.
Demehri, Farokh R. et al., "Development of an Endoluminal Intestinal Attachment for a Clinically Applicable Intestinal Lengthening Device," APSA2015 46th Annual Meeting Final Program, May 3, 2015, pp. 216-217.
Demehri, Farokh R. et al., "A Novel Therapy for Short Bowel Syndrome: Bowel Lengthening Device," Lifeline Letter, vol. XXXV, No. 6, Nov. 2014, pp. 1, 6, 7.
Utter, Brent Allen, "Technological Approaches for Investigating Mechanotransductive Enterogenesis: A Dissertation Submitted in Partial Fulfillment of the Requirements for the Degree of Doctor of Philosophy (Mechanical Engineering)," The University of Michigan, Oct. 13, 2014, pp. 1-242.
Extended European Search Report dated Dec. 6, 2017 regarding corresponding European Application No. 15795829.9, 13 pages.
Supplementary Partial European Search Report dated Aug. 20, 2018 regarding corresponding European Application No. 16740895.4, 12 pages.

* cited by examiner

FENESTRATED DECOUPLING SYSTEM FOR INTERNAL SELECTIVE ATTACHMENT TO SOFT TISSUE ORGANS

CROSS-REFERENCE TO RELATED APPLICATIONS

This application claims the benefit of U.S. Provisional Application No. 62/001,380, filed on May 21, 2014. The entire disclosure of the above application is incorporated herein by reference.

GOVERNMENT INTEREST

This invention was made with government support under FD-R-003787 awarded by the Food and Drug Administration. The government has certain rights in the invention.

FIELD

The present disclosure relates to device attachments to tubular members and, more particularly, relates to an expandable fenestrated decoupling system for internal selective attachment to hollow members, such as soft tissue organs.

BACKGROUND AND SUMMARY

This section provides background information related to the present disclosure which is not necessarily prior art. This section also provides a general summary of the disclosure, and is not a comprehensive disclosure of its full scope or all of its features.

Short bowel syndrome (SBS) is an often lethal medical condition characterized by the malabsorptive state of a patient who was born with intestinal atresia or has undergone massive small bowel resection to treat intestinal pathologies. The condition is challenging to manage and treat because of complications associated with parenteral nutrition, surgical bowel restructuring techniques, and transplants. As a result, mortality rates associated with SBS are as high as 38%. To provide an alternative to long-term parenteral nutrition reliance and surgical bowel lengthening, the present teachings provide a novel treatment device and method for short bowel syndrome based on mechanotransduction enterogenesis—the growth of tissue via application of a tensile load.

As one can appreciate, tissue-to-tissue and tissue-to-device attachment methods and devices are of great importance to a broad range of surgical applications including tissue approximation, wound closure, anastomoses, joint repair and replacement, osteo-distraction, long-gap esophageal repair, the prevention of stent migration, and the like. With respect to the tension-induced correction of short bowel syndrome (SBS), the ability to reliably and safely transfer load from an extending mechanism to the bowel wall is critical for success.

While the mechanotransduction approach to treating SBS is promising, the safe transfer of load from the extending mechanism to the bowel wall heretofore has remained a challenge. In prior research studies on mechanotransduction enterogenesis, two primary attachment mechanisms have been employed: 1) end abutting attachments—where a device is placed within an isolated segment of bowel whereby the ends of the bowel are sealed off to permit an internal device to press against the closed ends, thereby applying a tensile load—and 2) suture attachments—where sutures are used to surgically couple the device to the bowel wall. Although these attachment methods were suitable for research, they are not always reliable and may lead to other significant disadvantages that limit their use in clinical applications.

In order to realize the benefits of load-induced treatment in a clinical setting, there is a need for a tissue attachment device and method that attaches more reliably and safely. Ideally, a workable tissue attachment device and method would be able to achieve the following objectives:

transfer load from the extending device to the bowel wall without tissue slipping;

move freely through the bowel without inadvertently attaching to the bowel wall during implantation, removal, and other purposeful repositioning;

not cause ischemia (reduction of blood flood) on attached tissue, which may lead to compromised tissue;

not cause or require microscopic or macroscopic tearing, perforation, and/or other mechanical damage to tissue;

enable minimally invasive surgical procedures; and minimize the surgical manipulation of remnant small bowel.

Unfortunately, the end abutment and suture-based attachment methods described above do not meet many of these objectives, thereby limiting their clinical applicability.

According to the principles of the present teachings, an attachment system for attaching to an interior surface of a hollow member in both medical and non-medical applications is provided.

Although the present teachings will be described in connection with medical applications, and particularly in connection with the mechanical lengthening of soft tissue organs (e.g. bowels), it should also be understood that the principles of the present teachings may find utility in a wide variety of non-medical applications as will be discussed herein.

In some embodiments of the present teachings, an attachment system is provided for selectively attaching to an interior surface of a hollow member, which includes an expanding device selectively enlargeable from a first size to an enlarged second size, a friction enhancement disposed about the expanding device that is engageable with the interior surface of the hollow member when the expanding device is in the enlarged position, and a fenestrated decoupling system extending between at least a portion of the friction enhancement of the expanding device and the interior surface of the hollow member. The fenestrated decoupling system generally prevents contact of the friction enhancement with the interior surface of the hollow member when the expanding device is in the first size position and permits contact of the friction enhancement with the interior surface of the hollow member when the expanding device is in the enlarged position.

In some embodiments, the present teachings enable selective attachment of an elongation system to the inside of a generally tubular member, such as a soft tissue organ, which can be selectively attached and detached to permit application of longitudinal tensile loads while attached and permit slipping while detached. Conventional attachment systems are often permanent, instill injury to the soft tissue organ, and/or cannot apply significant longitudinal forces to facilitate tissue growth.

The present teachings were developed specifically to apply tensile loads and induce tissue growth in the small intestine, but are equally applicable to many other medical applications, including, but not limited to, esophageal growth, endovascular techniques, large intestine growth, blood vessels growth, other hollow organs growth, or endoscopy-type applications (where the application of traction is beneficial). The principles of the present teachings may also be applied to non-medical applications where attachment to and/or movement within tubular structures or irregularly shaped structures is desired. In each of these applications, the present teachings provide selective attachment and detachment capability.

While textured balloons have been used in the past for various endoscopic devices to hold a device in place within the intestines, the texture was necessarily limited to allow sliding of the device while the balloon was deflated. The innovation of the fenestrated decoupling system of the present teachings to selectively disengage the textured expanding device (e.g. balloon) enable a much deeper texture (i.e. increased frictional engagement) capable of applying much larger traction forces to the tissue. Without the fenestrated decoupling system of the present covering, the less deep mesh cannot provide sufficient traction against the soft tissue. The present teachings thus enable bowel or other organ extension/growth type uses and can greatly improve the capabilities of endoscopic devices to hold their positions, but still be easily moved and inserted when desired.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

However, according to the principles of the present teachings as illustrated in FIGS. 2 and 4-6, a fenestrated attachment system 220, such as an endoluminal balloon attachment mechanism, is provided that employs a fenestrated decoupling system 222. The fenestrated attachment system 220 is placed within the bowel lumen or other hollow member 100 and is capable of radially expanding, thereby coupling with the inner luminal surface 102 of the bowel or other interior surface 102 of the hollow member 100, to allow transfer of longitudinal tensile loads to the bowel wall or hollow member 100 and/or permit translation therethrough.

In some embodiments, fenestrated attachment system 220 can be used as part of an elongation system 200, such as a mechanotransduction enterogenesis device, for use in lengthening soft tissue (e.g. bowel). It should be understood, however, that the present disclosure is not to be regarded as requiring an elongation system or other component unless specifically claimed.

In some embodiments, elongation system 200 can define an elongated member 202 having opposing ends 204, 206 (i.e. distal and proximal ends). One or more of the opposing ends 204, 206 can comprise fenestrated attachment system 220, which will be described in greater detail herein. Internal to and/or between opposing ends 204, 206, elongation system 200 can comprise an extending mechanism 208 that is operable to longitudinally drive elongation system 200 between an extended position and a retracted position. In the extended position (see FIG. 4C), the opposing ends 204, 206 and the associated fenestrated attachment system 220 define a spaced-apart orientation. In the retracted position (see FIG. 4B), the opposing ends 204, 206 and the associated fenestrated attachment system 220 define a spaced-together orientation. In this way, in the retracted position, ends 204, 206 are in their narrowest configuration and, in the extended position, ends 204, 206 are in their widest configuration. As will become apparent, if both fenestrated attachment systems 220 are engaged with the interior surface 102 of the hollow member 100, movement between the retracted position and the extended position can result in application of a tensile force to the hollow member 100 proportional to the force exerted by extending mechanism 208. Likewise, if only one fenestrated attachment system 220 is engaged with the interior surface 102 of the associated hollow member, movement between the retracted position and the extended position can result in application of a translational force.

In some embodiments, extending mechanism 208 can comprise a reciprocating linear hydraulic actuator. However, it should be understood that a wide variety of drive actuation devices can be used in connection with extending mechanism 208, including hydraulic, pneumatic, push-cable driven, screw-driven, SMA wire, SMA helical spring, SMA-driven ratchet, thermal expansion/phase change actuator driven, electromagnetic actuator (solenoid, linear stepper motor, rotary screw drive motor). For additional detail relating to these actuation systems, reference should be made to commonly-owned U.S. Pat. Nos. 7,722,560 and 8,268,009, which is hereby incorporated and made a part of the present application.

In some embodiments, extending mechanism 208, when configured as a reciprocating linear hydraulic actuator, is based on a "payout" approach. By repeating the operation cycle, the length of tissue growth induced is limited only by the number of times extending mechanism 208 is cycled rather than the stroke of extending mechanism 208. In some embodiments, extending mechanism 208 can be concealed and/or protected using a sheath 210, such as a thin silicone sheath, to protect extending mechanism 208 from associated environmental contaminants and to facilitate operation. For example, when the device is retracted, the thin silicone sheath prevents the bowel from pleating between the attachments, promoting the repositioning of bowel relative to the attachments.

In some embodiments, a compliant tissue guide 212 can be disposed on a distal side of end 204 or 206. Compliant tissue guide 212 can be used to facilitate insertion and articulation of elongation system 200 within the bowel lumen or hollow member 100 to prevent kinking around of the device and becoming ischemic. One or more silicone tubes connecting the device to external syringes can be used for actuation of the extending mechanism 208.

To facilitate the selective attachment and detachment of elongation system 200 from the bowel lumen or other hollow member 100, fenestrated attachment system 220 comprises an expanding device 224 (e.g. balloon) disposed on at least one end 204, 206. In some embodiments, expanding device 224 is enlargeable between a deflated position (first size position) and an inflated position (second size position), whereby the inflated position is sufficiently large to permit mechanical engagement with the interior surface 102 of the hollow member 100 (i.e. bowel lumen). It should be understood that in some embodiments, the size of the inflated position must be sufficiently large to further accommodate any resultant enlargement of the hollow member in response to application of the inflation force. Likewise, it should be understood that in some embodiments, the size of the deflated position must be sufficiently smaller to permit disengagement of fenestrated attachment system 220 from the interior surface 102 of hollow member 100, at least when used in conjunction with fenestrated decoupling system 222.

In some embodiments, fenestrated attachment system 220 further comprises a friction enhancement or texture 226. In some embodiments, friction enhancement 226 can comprise application of an abrasive texture generally surrounding expanding device 224 that is capable of expanding during inflation of expanding device 224 and retracting during deflation of expanding device 224. In some embodiments, it has been found that an open-cell matrix, such as a 3M, Scotch-Brite Dobie, is useful. In some embodiments, friction enhancement 226 can comprise a fabric material structure surrounding expanding device 224. The fabric material structure can include one or more fibers knitted into a series of interlocked loops such that the knitted fabric can expand and contract along with expanding device 224. The loops can engage the interior surface 102 of the hollow member 100. In some embodiments, the fibers can include a flat ribbon such that the edges of the flat ribbon engage with the interior surface of the hollow member. In some embodiments, the friction enhancement 226 can include a plurality of bristles fixed to expanding device 224 engageable with the interior surface of the hollow member. In some embodiments, the friction enhancement 226 can include a plurality of loops fixed to the expanding member which engage the interior surface of the hollow member. Moreover, in some embodiments, the friction enhancement 226 comprises a plurality of scales, suction cups, and/or ridges fixed to the expanding device 224 which engage with the interior surface of the hollow member.

However, it was found that in some applications, friction enhancement 226 may not reliably disengage from interior surface 102 of hollow member 100 even after expanding device 224 is deflated and friction enhancement 226 is in the retracted position. Failure to disengage from interior surface 102 may inhibit further insertion, removal, and/or purposeful repositioning of the device. Accordingly, fenestrated decoupling system 222 can be employed about friction enhancement 226 to encourage disengagement of friction enhancement 226 from interior surface 102 upon deflation of expanding device 224. In some embodiments, fenestrated decoupling system 222 can comprise a plurality of bands 228 being disposed longitudinally along friction enhancement 226 at radial positions radially thereabout. In some embodiments, the plurality of bands 228 are comprises of elastic bands, which can be made of a monofilament material. The plurality of bands 228 can be retained by a pair of ring members 230 disposed at opposing sides of fenestrated attachment system 220 that permit the plurality of bands 228 to pass there over and be captured and retained within fenestrated attachment system 220.

During operation, in some embodiments, fenestrated decoupling system 222 is operable to expand to accommodate inflation of expanding device 224 and, by association, enlarge friction enhancement 226, thereby permitting friction enhancement 226 to engage the interior surface 102 of hollow member 100. Once friction enhancement 226 is operably engaged with interior surface 102, extending mechanism 208 of elongation system 200 can be actuated. Conversely, once actuation is complete, expanding device 224 can be deflated and, by association, retract friction enhancement 226. This permits friction enhancement 226 to retract. The plurality of bands 228 of fenestrated decoupling system 222 can similarly retract. Retraction of friction enhancement 226 to a size smaller than retraction of the plurality of bands 228 of fenestrated decoupling system 222 can permit the plurality of bands 228 to disengage interior surface 102 of hollow member 100 from friction enhancement 226, thereby permitting insertion, removal, and purposeful repositioning of the device.

In some embodiments, fenestrated decoupling system 222 can comprise a non-expanding device that is sufficiently fenestrated to permit expanding device 224 and friction enhancement 226 to extend through the fenestrated portions to a position exterior of fenestrated decoupling system 222 thereby engaging interior surface 102. Upon deflation of expanding device 224, expanding device 224 and friction enhancement 226 can collapse within a volume defined by fenestrated decoupling system 222, thereby disengaging from interior surface 102.

Fenestrated attachment system 220 represents a large step forward in the development of a clinically relevant device for correcting SBS for two key reasons. Firstly, the architecture of the fenestrated decoupling system 222 enables minimally invasive implantation and removal surgeries, greatly reducing the cost, recovery time, chance of surgical complications, and improving the overall quality of patient care. Secondly, the fenestrated decoupling system 222 induces high net bowel growth in the limited space within the peritoneal cavity, potentially enabling the treatment of very severe cases of SBS in infants and children.

Background Regarding Experimental Evaluation of Various Attachments

It is believed that a discussion relating to the development of the present teachings is useful to the overall understanding of the principles of the present invention. Accordingly, the tendency of simple dilating attachments to either not sufficiently attach or not sufficiently detach is demonstrated in a series of acute in-vivo experiments involving several balloon-style attachments with varying degrees of texture.

Smooth and Textured Balloons

Figure 1A:
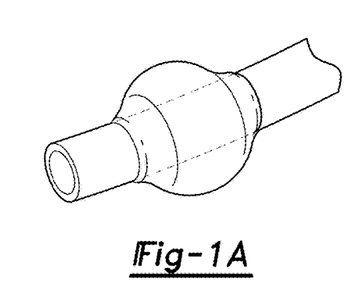
FIGS. 1A-1G are photographs illustrating a series of dilation prototypes.
Figure 1B:
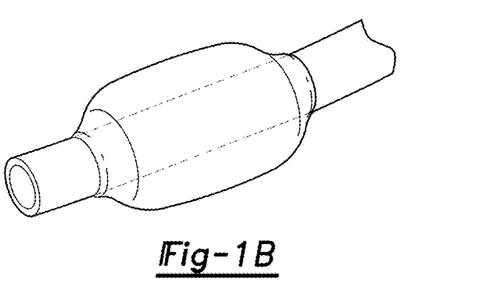
Figure 1C:
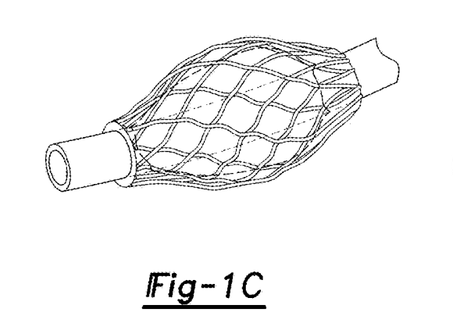
Figure 1D:
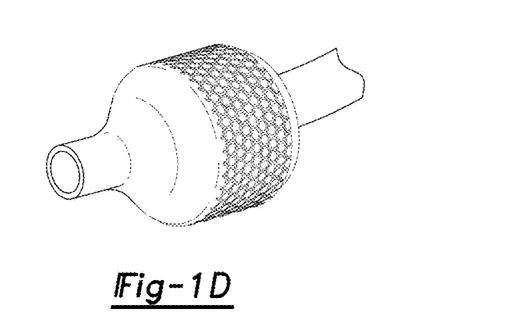
Figure 1E:
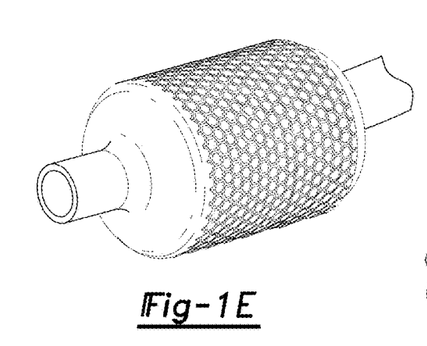
Figure 1F:
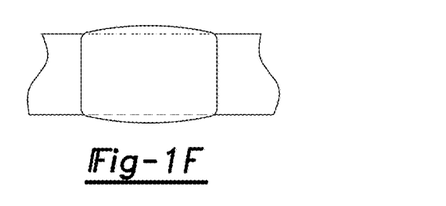
Figure 1G:
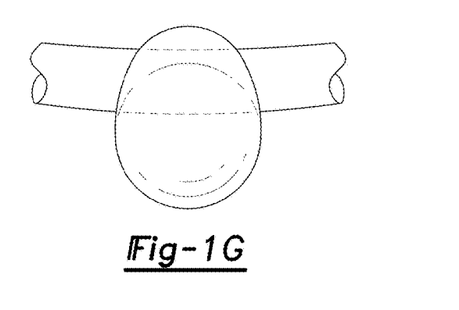

A range of balloons, with and without texture, were evaluated in acute in vivo experiments to determine their ability to apply traction on the small bowel without slipping and without causing ischemia. Many concepts were fabricated based on the various permutations of balloon type, the presence of a texturing material, and the type of texturing material. The balloons were taken from endotracheal (ET) tubes (Kimberly-Clark: Microcuff, 7 mm ID tube, and Sheridan/HVT 9 mm ID tube), and Foley urinary catheters (Bard Medical: BARDEX 5 cc Balloon, 30FR catheter). In some trials, the balloons were textured by the application of loose mesh bagging material (FIG. 1C) or abrasive material taken from scrubbing sponges (FIGS. 1D and 1E). Of these prototypes, several were eliminated early in the experiments. For example, the Foley urinary catheters did not inflate symmetrically about the axis of the catheter (FIG. 1G), like the ET tubes (FIGS. 1A and 1B). Additionally, the loose mesh bagging material (FIG. 1C) did not make any significant impact on the gripping performance of the balloon attachments. Because of this, only the ET tube balloons were evaluated with (FIGS. 1D and 1E) and without (FIGS. 1A and 1B) the abrasive material from scrubbing sponges as a texturing agent.

Experimental Procedure

To evaluate the attachment approach, the initially deflated balloons were inserted into the small bowel lumen of live porcine models, inflated to a measured pressure from 0 to 60 mmHg, and then manually pulled on with a tension measuring probe with increasing tension until the balloon slipped. The condition of the balloon slipping was evaluated visually during each trial, using the vasculature of the small bowel as reference points, and was defined as any longitudinal motion of the attachment relative to the bowel lumen. The health of the small bowel tissue was grossly determined by visually checking the tissue for any signs of macroscopic mechanical disruption and acute ischemia, which was indicated by tissue blanching.

Results

Figure 8:
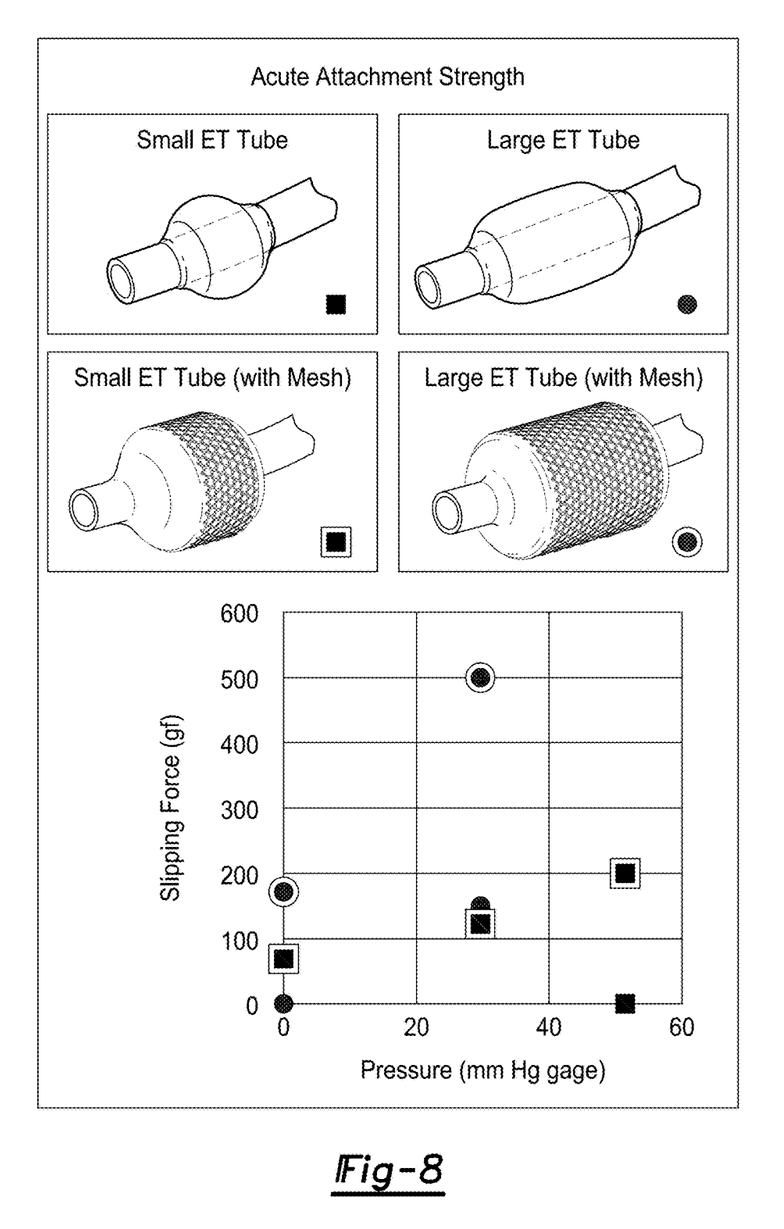
FIG. 8 is a graph illustrating acute attachment strength for various embodiments.

Results from these experiments are plotted in FIG. 8. Four different prototypes were evaluated: a large ET tube balloon with and without texture, and a small ET tube with and without texture. The basic trends of this experiment were intuitive: the application of greater pressure, the greater size of the balloon, and the presence of the gripping material all increased the slipping force of the attachments. Interestingly, the abrasive scrubbing material made a very large impact on the performance of the attachments without mechanically significantly scraping the delicate mucosal layer of the bowel segments. This result was determined by the lack of mucosal scrapings embedded in the material when its balloon was removed from the bowel segment. Furthermore, because the addition of the scrubbing material greatly reduced the need for the balloons to apply high pressure in order to attach, the pressure applied to the small bowel and therefore the risk of acute ischemia was significantly reduced.

Unfortunately however, the application of the scrubbing material also made both balloon sizes have a significant gripping load even when the balloons were completely deflated. In fact, the large balloon could not be inserted without using a plastic sheath between the material and the bowel wall. This is a disadvantage because these attachments would be difficult to surgically implant and remove because they do not slide though the tissue.

Fenestrated Decoupling System

In the acute in vivo experiment of textured balloons, the approach was very promising with respect to their ability to grip the bowel wall when inflated. When inflated and attached, the tissue with which the balloons made contact remained well perfused with blood. Thus, the risk of ischemia with the approach is minimized.

Unfortunately however, the abrasive material used to texture the balloons made the attachments also grip well even when the balloons were deflated. In other words, as the textured balloons were deflated, the bowel lumen similarly constricted, thereby remaining engaged with the texture. This is an important disadvantage because an extending device using these attachments could potentially be difficult and unsafe to implant, reposition, and remove. Thus, a solution to cover the balloons/texture when deflated and uncover the balloons/texture when inflated was developed.

Figure 2A:
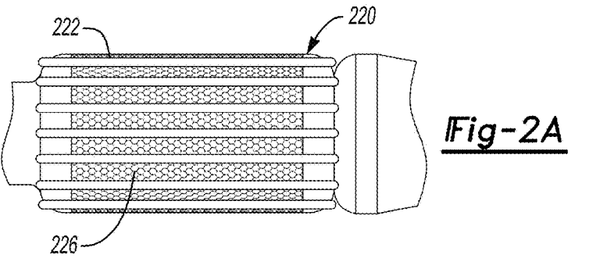
FIGS. 2A-2B are side views illustrating the fenestrated decoupling device according to the present teachings in a retracted and expanded position, respectively.
Figure 2B:
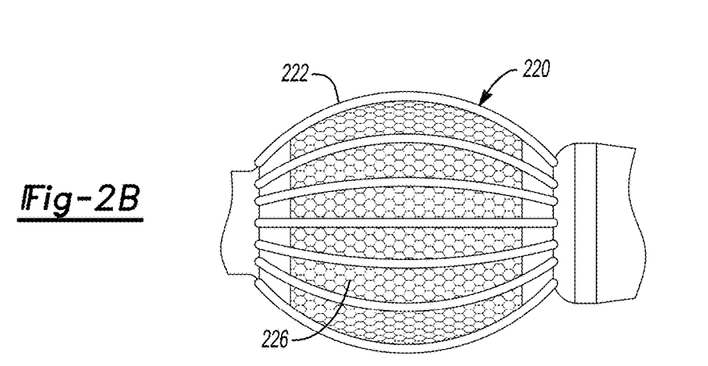

The attachment prototypes, shown in FIGS. 2A and 2B, were modified by the addition of elastic bands suspended over the texture of balloon by machined Delrin end caps. The Delrin end caps have a circular array of holes through which the elastic cord is placed. When the balloon is deflated FIG. 2A, the function of the bands is to prevent the bowel mucosal from making contact—thus enabling the attachments to be implanted, repositioned, and removed safely with ease. When the balloon is inflated (FIG. 2B), the spacing of the elastic bands becomes less dense, allowing the tissue to making contact with the textured balloons and enabling the attachments to transfer load effectively.

To validate this functionality and evaluate the reliability and safety of using these attachments clinically, a one week in vivo experiment was conducted where the attachments were cycled between their inflated and deflated states. While inflated, the balloons were separated by the single stage linear hydraulic device for several hours. Then, the balloons were deflated and the reciprocating hydraulic device was retracted for several hours. This cycle of tensioning and relaxing the small bowel segment was repeated for 8 hours a day over the course of one week. Results from the one-week in vivo study indicated that the attachments were a success.

One major concern with their use was that the texturing material would become saturated with debris over time, greatly reducing their attachment performance. To evaluate this failure mode, the attachment and detachment forces were evaluated at the explant with a load sensor. With the balloons of each attachment deflated, the fenestrated decoupling device could move though the bowel lumen with ease, with the force required to initiate motion being measured at approximately 120 gf (value is for both attachments). With a single attachment engaged, the measure force exceeded 450 gf, saturating the measurement system. Although the texturing material appeared to be potentially clogged, the attachment performance was no less than that at the start of the implantation period. Additionally, this allowed distraction to be applied without the balloon slipping.

Figure 3:
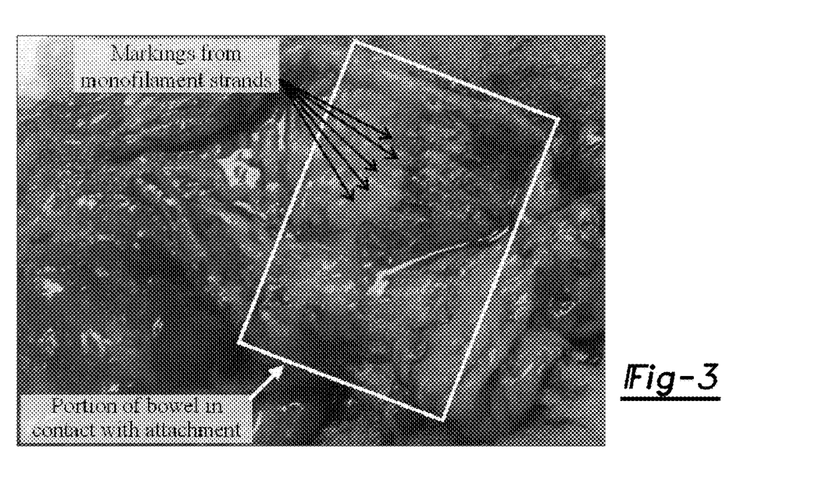
FIG. 3 is a photograph illustrating bowel tissue.
Figure 4A:
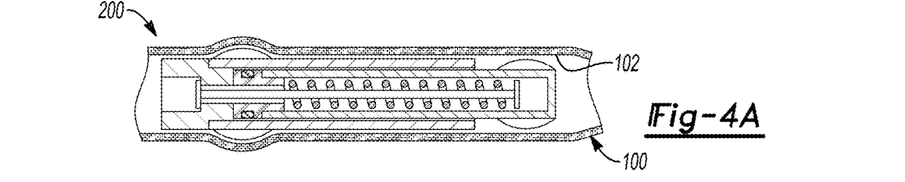
FIGS. 4A-4E illustrate a series of cross-sectional schematic views of actuation of an elongation system according to the principles of the present teachings.
Figure 4B:
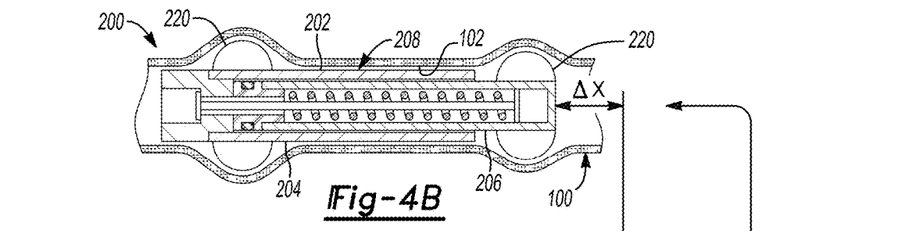
Figure 4C:
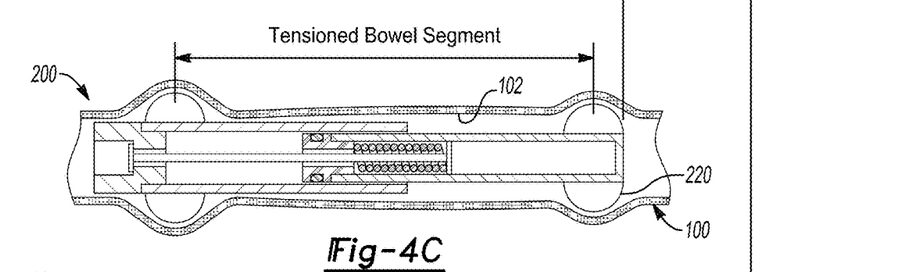
Figure 4D:
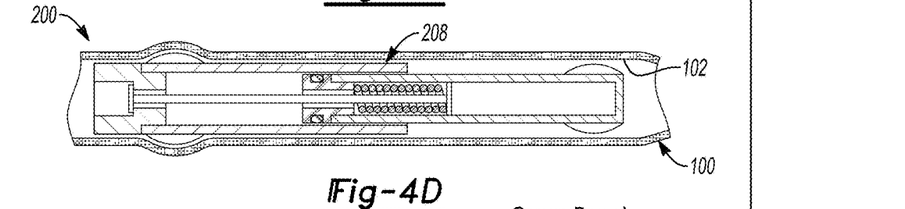
Figure 4E:
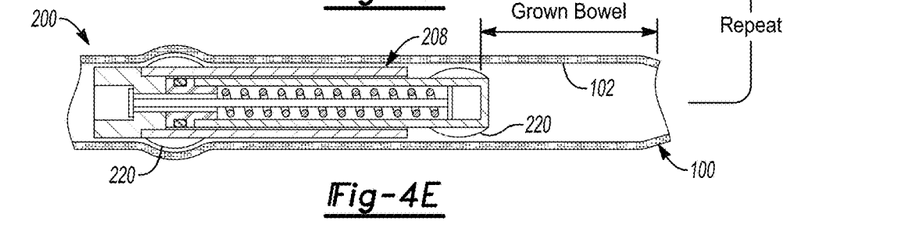

The other concern associated with the longer term use of these attachments was their effect on the health of the bowel mucosal, given the abrasive nature of the texturing material. FIG. 3 shows the portion of bowel tissue that the attachment was in contact with for the duration of the implantation. Although parallel line imprints from the monofilament strands were observed and there was mild tissue inflammation, the tissue was in good health and had an intact mucosal lining.

Fenestrated Attachment System Testing and Validation

As described herein, although the device can be coupled to the bowel wall using a wide range of expansion mechanisms, in some embodiments, the device can employ a reciprocating linear hydraulic device as illustrated in FIGS. 4A-4E. The concept consists an outer housing and an inner housing that displace relative to each other when hydraulically driven, two attachments that are capable of gripping and releasing the bowel wall, a compression spring which retracts the fenestrated decoupling device, a constraining rod that limits the motion of the inner housing relative to the outer housing, and a hydraulic line adapter. The hydraulic line connects to an external syringe from which water can be injected into the fenestrated decoupling device. In addition to the hydraulic line, one to two pneumatic lines connect each attachment to an external syringe to inflate and deflate the balloons.

The payout operation with respect to the reciprocating linear hydraulic device with Dilating Fenestrated decoupling system balloon attachments is described in five stages and illustrated in FIGS. 4A-4E. In the first, nominal, or "implanting stage," the fenestrated decoupling device is retracted and the attachments are deflated, disengaging them from the tissue. In the "attaching stage," the attachments are inflated from external syringes through pneumatic lines, pressing the abrasive mesh material into the bowel mucosal and thus gripping the tissue. In the "tensioning stage," water injected from an external syringe through the hydraulic lines enters the inner and outer housings of the sealed device, forcing the displacement of the inner housing relative to the outer housing. As more water is injected from the external syringe, the constraining rod and seal mount compress the spring until it reaches its solid length. At this point, further device expansion is not possible and the bowel segment between the attachments is tensioned. The expansion of the fenestrated decoupling device and engagement of the attachments is maintained for a time sufficient to induce bowel growth prior to disengaging the attachments (venting the balloons to atmospheric pressure) in stage four, the "detaching stage." Ideally at stage four, the bowel has grown and does not reduce in length when the attachments are disengaged. In the "paying out" stage, the pressure on the hydraulic line is reduced to atmospheric pressure and the compression spring retracts the fenestrated decoupling device, leaving the grown tissue distal to the distal attachment. The completion of stage five returns the fenestrated decoupling device to its nominal position, and the cycle is repeated multiple times during the distraction period of the implantation. Each time the cycle is completed, the amount of bowel growth induced is accumulated without the length of the fenestrated decoupling device accumulating. Therefore, the growth of the small bowel is not limited by the constrained space of the peritoneal cavity. This represents a very important advantage compared to the other conceptual expansion approaches for treating SBS—an advantage that would not be possible without the ability of the attachments to disengage and reengage the bowel mucosal.

Prototype Attachment Integration

Figure 5A:
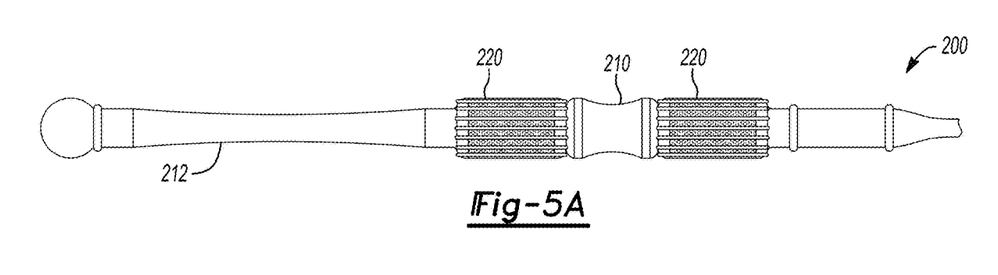
FIGS. 5A-5C are side views illustrating the elongation system according to the principles of the present teachings.
Figure 5B:
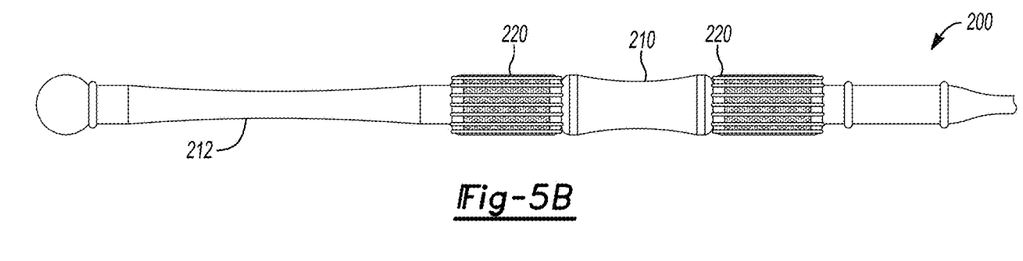
Figure 5C:
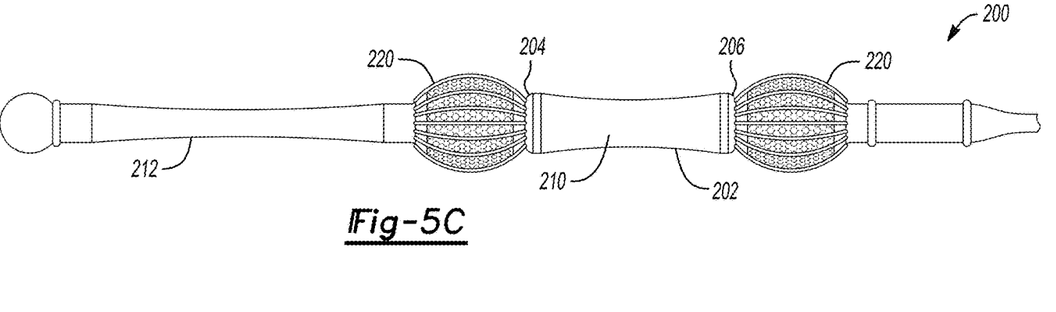

The extension mechanism was integrated with a distal and proximal tissue attachment with the capability to both attachment and detach from the bowel wall, enabling the payout operation. FIGS. 5A-5C shows the components of the integrated prototype prepared for in vivo experiments, which includes a compliant device extension made from 18 Fr latex tubing, the distal and proximal attachments, a thin silicone sheath held between the attachments, and 4 controls lines for the fenestrated decoupling device extension (water), the flush (water), and the independently inflated attachment balloons (air).

Figure 6:
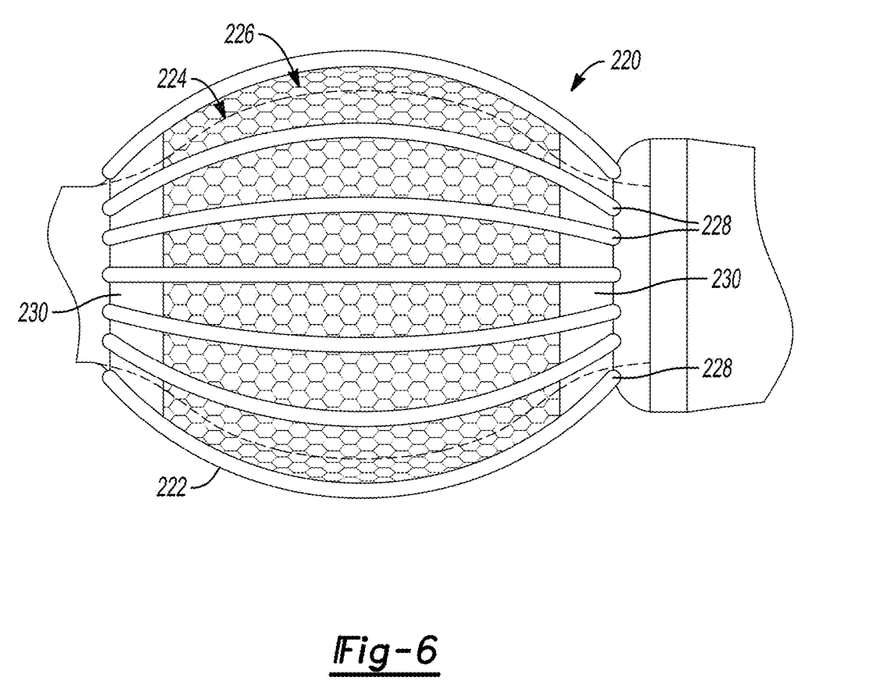
FIG. 6 is a side view illustrating the fenestrated decoupling device according to the principles of the present teachings.

A detailed view of the inflated distal attachment is shown in FIG. 6. Each attachment is composed of two machined Delrin filament guides, knitted abrasive texturing material taken from the outer surface of a kitchen scrubbing pad (3M Scotch-Brite "Dobie"), a balloon taken from a Foley catheter (Bard® BARDEX 30 Fr 5 cc), and a single length of clear elastic monofilament. To assemble, the balloon is mounted directly on the extending mechanism, with the monofilament guides on each end. The abrasive material is then placed over the balloon and held in place by the monofilament line, which is threaded through the guides.

The total length of the fenestrated decoupling device (excluding the lines) is approximately 26 cm, although when retracted the attachment-to-attachment distance is 6 cm. However, it should be understood that in some embodiments the fenestrated decoupling device can define alternative sizes and configurations. By way of non-limiting example, in some embodiments, the total length of the fenestrated decoupling device can be in the range of about 4 cm to about 50 cm. When the attachments are deflated, the maximum outer diameter of the fenestrated decoupling device is 16 mm (⅝ in), which is expands to 27 mm when the attachments are inflated with 20 cc of air. Likewise, however, the maximum outer diameter of the fenestrated decoupling device can be any size, shape, or configuration. By way of non-limiting example, in some embodiments, the maximum outer diameter of the fenestrated decoupling device can be in the range of about 5 mm to about 10 cm. The fenestrated decoupling device extends by 3.4 cm when actuated by the hydraulic line with approximately 2 cc of water, displacing the midpoints of the attachments from 6 to 9.4 cm (56% expansion). Finally, in some embodiments, the fenestrated decoupling device can extend in the range of about 2 cm to about 50 cm.

In Vivo Experimental Growth Study

To validate the operation of the Reciprocating Linear Hydraulic Device with Dilating Fenestrated decoupling system Attachments in vivo, and more importantly, to demonstrate that the attachments make a payout approach to growing small bowel achievable, an in vivo study was conducted with a porcine animal model. The ultimate goal of the experiment was to increase a length of bowel by an amount that is greater than the stroke of the fenestrated decoupling device, because this would establish the feasibility of the payout approach. In the following section, the experimental procedure and results are discussed.

In Vivo Experiment Procedure

The procedures of the in vivo experiment consist of the procedure for the surgical implantation of the fenestrated decoupling device, the fenestrated decoupling device expansion procedure, and the tissue analysis and growth measurement plan. The compact design of the fenestrated decoupling device and the controlled intraluminal attachments enable less invasive implantation approaches than other attachment approaches allow. For example, the fenestrated decoupling device could potentially be placed into the continuous GI tract through a gastrostomy and guided into the small bowel with an endoscope placed through the upper GI tract. More optimally, with some refinement the fenestrated decoupling device could potentially be placed through the upper GI tract and require little to no surgical tissue manipulation of the small bowel.

Surgical Implantation Procedure

As shown in FIGS. 7A-7D, the reciprocating linear hydraulic device was implanted into a Roux limb rather than placed in the continuous GI tract. The Reciprocating Linear Hydraulic Device was not fixed relative to the Roux limb by sutures and was free to slide through the bowel lumen.

Figure 7A:
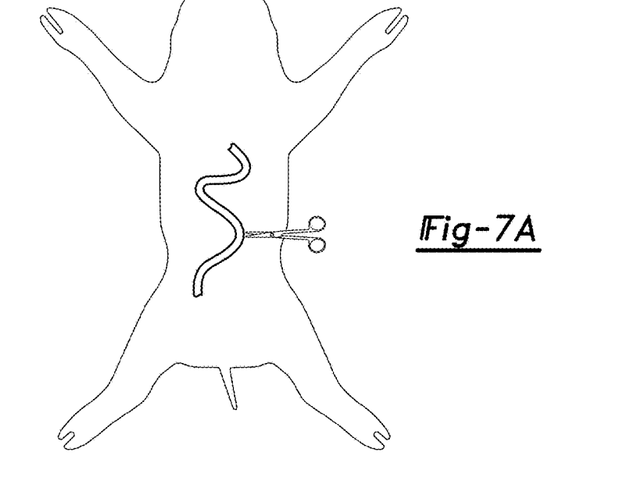
FIGS. 7A-7D is a series of schematic views illustrating surgical implantation procedures in according to the principles of the present teachings.
Figure 7B:
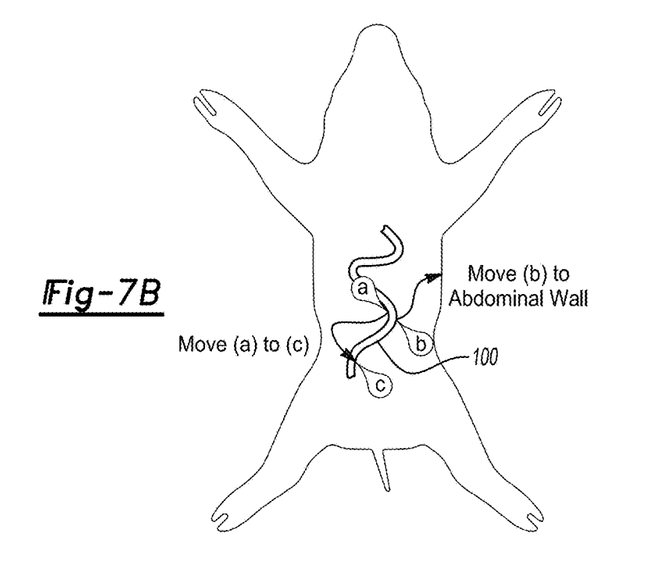
Figure 7C:
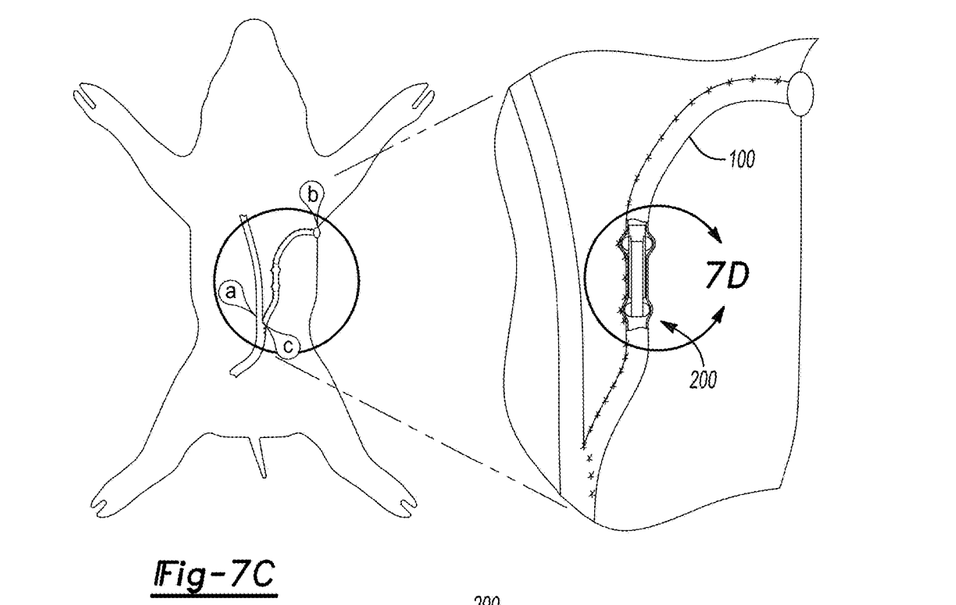

The surgery began with a 15 cm midline incision to open the abdominal cavity of the porcine model. The small bowel was manipulated to determine the flow direction of enteral contents and to locate the Ligament of Treitz, which marks the start of the small intestine. Approximately 60 cm along the length of small bowel from the Ligament of Treitz the small bowel was cut, creating two open ends of bowel labeled (a) and (b), as shown in FIG. 7B. Approximately 60 to 75 cm along the length of bowel from (b), an end-to-side anastomosis was created, connecting (a) to (c) and restoring the continuity of the GI tract. The segment of small bowel from (b) to (c), or Roux limb, was no longer in the continuity of the GI tract and would not pass ingested contents, however, the health of the Roux limb was maintained by the blood supply from the intact mesentery. During the creation of the Roux limb, the Reciprocating Linear Hydraulic Device was sterilized by soaking it in a liquid sterilant (Metrix, Metricide®) for the manufacturer recommend time of 40 minutes. After sterilization, the fenestrated decoupling device was thoroughly rinsed with sterile saline to prevent any sterilant from getting into the surgical field, with special care was taken to completely remove sterilant from the mesh material of the attachments. The Reciprocating Linear Hydraulic Device was inserted, compliant tissue guide first, into the open end of the Roux limb. A stoma, or surgically created opening, was made in the skin and fascia of the abdomen, and the Roux limb was secured to the stoma at the fascia and skin. The final steps of the surgery were to route the hydraulic and pneumatic lines through the Roux limb, connect the external syringes to the lines, and secure the external syringes and control line to the center of the porcine model's back. At the conclusion of the implantation, the Roux limb was 70 cm in length and the fenestrated decoupling device was implanted approximately 25 cm from the stoma.

Device Expansion Procedure

During the day of the operation, no extension of the fenestrated decoupling device or inflation of the attachments was completed to allow the animal to rest. For the next six days post operation, the five-stage operation illustrated in FIGS. 4A-4E was repeated four times per day, at 8 am, 12 pm, 4 pm, and 8 pm. At 8 am, the fenestrated decoupling device is already contracted and the attachments are disengaged from the prior day. First, both attachments are engaged by inflating the distal and proximal balloons with approximately 15 mL of air. Then, the fenestrated decoupling device is extended 3.4 cm by the injection of 2 mL of water into the hydraulic line, putting the bowel segment between the attachments under tension. Over the following four hours, the bowel tension decreases due to some combination tissue growth, tissue slipping, and/or viscoelastic effects until the next device expansion at 12 pm. At both 12 pm and 4 pm, the payout operation is continued by disengaging both attachments (deflating the balloons), retracting the fenestrated decoupling device (drawing 2 mL out of the hydraulic line), reengaging both attachments, and extending the fenestrated decoupling device. Finally, at 8 pm each day, the attachments are disengaged and the fenestrated decoupling device is retracted, allowing the bowel to rest for 12 hours. The fenestrated decoupling device was removed on the 7th post-operative day during the explant surgery.

Tissue Measurement Plan

Figure 7D:
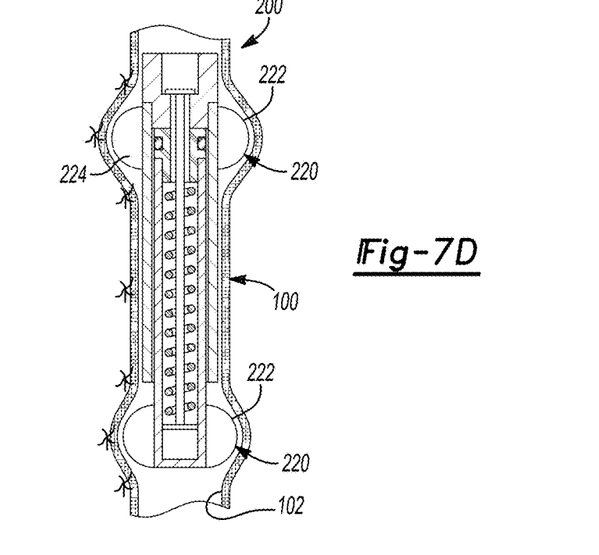

The net growth of the bowel in the Roux limb was evaluated using marking sutures onto which radiopaque stainless steel clips were attached. At the implant surgery, thirty five marking sutures were evenly placed along the entire length of the Roux Limb and three sutures (placed 2 cm apart) were placed on the normal fed bowel distal to the anastomosis. Initially, the markers on the Roux limb were also placed 2 cm apart. This marking approach was taken, because even if the implanted device changes position along the Roux Limb, measurements of the distance between the sutures at the explant can be used to estimate the net growth of the tissue. FIG. 7D shows the 11th through the 17th (numbered from the stoma to the anastomosis) suture as they were aligned with the fenestrated decoupling device at the implant.

In Vivo Experiment Results: Tissue Growth Analysis

The extent of macroscopic tissue growth can be estimated by comparing the tissue marking suture measurements from the explant relative to the implant. FIG. 7D shows the placement of the fenestrated decoupling device relative to the sutures at the implant and the explant, and the change in marker spacing between the markers that were originally on the fenestrated decoupling device. Initially, the sutures were placed 2 cm apart, making the distance from the 11th to the 17th marking suture 12 cm. At the explant, the total tissue length from the 11th to the 17th marking suture 16 cm to 18.8 cm, depending on whether a marking suture slipped out of the tissue distal to the 15th marking suture. Unfortunately, it was not possible to determine whether this particular suture slipped out of the tissue or not during the distraction period with any certainty. Best case scenario, the tissue grew approximately 6.8 cm, which is twice the stroke of the Reciprocation Linear Hydraulic Device. In this case, lengthening the tissue by twice the stroke of the fenestrated decoupling device very strongly demonstrates that the pay-out approach to tissue lengthening is feasible. In the worst case scenario, the tissue grew 4 cm, which is 120% of the fenestrated decoupling device stroke and still suggests that the payout approach is feasible. In either case, there are some definitive results that can be made from tracking the marking sutures. First, the tissue segment from suture 11 to suture 15 expanded from 8 cm at implant, to 12 cm at explant, growing by 50%. And second, the tissue marked by sutures 16 and 17 was successfully paid out from the fenestrated decoupling device. These two definitive results strongly suggest that the Dilated Fenestrated decoupling system Attachments were able to both apply bowel tension and slide through the bowel lumen, and that the payout approach to bowel lengthening enabled by these attachments is feasible.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An attachment system for selectively attaching to an interior surface of a hollow member, the attachment system comprising:
    an expanding device selectively enlargeable from a first size position to a second size position, said second size position being larger than said first size position, said expanding device having an outer surface, said outer surface having a friction enhancement disposed directly thereon, said friction enhancement being directly engageable with the interior surface of the hollow member when said expanding device is in said second size position; and
    a fenestrated decoupling system generally surrounding said friction enhancement of the expanding device and being positionable between at least a portion of said friction enhancement of said expanding device and the interior surface of the hollow member, said fenestrated decoupling system configured to inhibit contact of said friction enhancement with the interior surface of the hollow member only under direct influence of the size of said expanding device in said first size position, said fenestrated decoupling system configured to permit contact of said friction enhancement with the interior surface of the hollow member only under direct influence of the size of said expanding device in said second size position.

2. The attachment system according to claim 1, further comprising:
    a pair of said expanding devices disposed on opposing ends of an elongated member, said elongated member being actuatable between a retracted position and an extended position to permit application of a tensile load to the hollow member when said expanding device is in said second size position.

3. The attachment system according to claim 1, wherein said expanding device comprises an inflatable member.

4. The attachment system according to claim 1, wherein said expanding device comprises a pneumatic member.

5. The attachment system according to claim 1, wherein said expanding device comprises a hydraulic member.

6. The attachment system according to claim 1, wherein said friction enhancement comprises a fabric material structure surrounding said expanding device and comprising a fiber knitted into a series of interlocked loops such that said knitted fabric can expand and contract along with said expanding device and said loops engageable with the interior surface of the hollow member.

7. The attachment system according to claim 6, wherein said fiber comprises a plurality of fibers knitted into said fabric material structure.

8. The attachment system according to claim 7, wherein at least one of said plurality of fibers is a flat ribbon such that edges of said flat ribbon is engageable with the interior surface of the hollow member.

9. The attachment system according to claim 1, wherein said friction enhancement comprises a plurality of bristles fixed to said expanding member engageable with the interior surface of the hollow member.

10. The attachment system according to claim 1, wherein said friction enhancement comprises a plurality of loops fixed to said expanding member which is engageable with the interior surface of the hollow member.

11. The attachment system according to claim 1, wherein said friction enhancement comprises a plurality of scales fixed to said expanding member which is engageable with the interior surface of the hollow member.

12. The attachment system according to claim 1, wherein said friction enhancement comprises a plurality of suction cups fixed to said expanding member which is engageable with the interior surface of the hollow member.

13. The attachment system according to claim 1, wherein said friction enhancement comprises a plurality of ridges fixed to said expanding member which is engageable with the interior surface of the hollow member.

14. The attachment system according to claim 1, wherein said fenestrated decoupling system comprises a plurality of fenestrated elastic bands having a spaced-apart configuration extending generally along a longitudinal length of said expanding device.

15. The attachment system according to claim 1, wherein said fenestrated decoupling system is extendable about said expanding device in said second size position.

16. The attachment system according to claim 1, wherein said fenestrated decoupling system is operable to disengage the interior surface of the hollow member from the friction enhancement in the first size position.

17. The attachment system according to claim 1 wherein said expanding device is smaller than said fenestrated decoupling system in said first size position.

* * * * *

UNITED STATES PATENT AND TRADEMARK OFFICE
CERTIFICATE OF CORRECTION

PATENT NO. : 10,159,486 B2
APPLICATION NO. : 14/718175
DATED : December 25, 2018
INVENTOR(S) : Utter et al.

Page 1 of 1

It is certified that error appears in the above-identified patent and that said Letters Patent is hereby corrected as shown below:

On the Title Page

Page 3, Column 1, Other Publications, Line 19, delete "Lenghthening" and insert --Lengthening-- therefor Page 3, Column 1, Other Publications, Line 23, delete "Lenthened" and insert --Lengthened-- therefor In the Claims Column 15, Claim 17, Line 8, after "claim 1", insert --,--

Signed and Sealed this
Eighteenth Day of June, 2019

Andrei Iancu
*Director of the United States Patent and Trademark Office*